US006812329B2

(12) United States Patent
Nagata

(10) Patent No.: US 6,812,329 B2
(45) Date of Patent: Nov. 2, 2004

(54) CONSTRUCTION AND CHARACTERIZATION OF MONOCLONAL ANTIBODIES AGAINST WESTERN EQUINE ENCEPHALITIS VIRUS

(75) Inventor: Leslie P. Nagata, Medicine Hat (CA)

(73) Assignee: Her Majesty the Queen in right of Canada, as represented by the Minister of National Defence, Ottawa (CA)

( * ) Notice: Subject to any disclaimer, the term of this patent is extended or adjusted under 35 U.S.C. 154(b) by 186 days.

(21) Appl. No.: 09/793,606

(22) Filed: Feb. 27, 2001

(65) Prior Publication Data

US 2002/0141997 A1 Oct. 3, 2002

(51) Int. Cl.[7] .......................... C07K 16/00; C12P 21/08
(52) U.S. Cl. ................. 530/388.3; 435/339; 424/218.1
(58) Field of Search ...................... 530/388.3; 435/339; 424/218.1

(56) References Cited

PUBLICATIONS

Hunt, A. R., and J. T. Roehrig, 1985, "Biochemical and biological characteristics of epitopes on the E1 glycoprotein of western equine encephalitis virus", Virol. 142:334–346.*
Long, M. C., et al., 2000, "Construction and characterization of monoclonal antibodies against western equine encephalitis virus", Hybridoma 19(2):121–127.*
Long, M. C., et al., 2001, "Pharmacokinetics study of a novel chimeric single–chain variable fragment antibody against western equine encephalitis virus", Hybridoma 20(1):1–10.*
Calisher, C. H., et al., 1986, "Specificity of Immunoglobulin M and G antibody responses in humans infected with eastern and western equine encephalitis viruses: application to rapid serodiagnosis", J. Clin. Microbiol. 23(2):369–372.*
Day, J. F., et al., 1996, "Antibodies to Arthropod–borne encephalitis viruses in small mammals from southern Florida", J. Wildlife Dis. 32(3):431–436.*
Donald J. Netolitzky et al., "Complete Genomic RNA Sequence of Western Equine Encephalitis Virus and Expression of the Structural Genes," Journal of General Virology, V81, pp. 151–159 (2000).
Melissa C. Long et al., "Construction and Characterization of a Novel Recombinant Single–Chain Variable Fragment Antibody Against Western Equine Encephalitis Virus," HYBRIDOMA, V19, No. 1, pp. 1–13 (2000).

Kiichi Yamamoto, "Properties of Monoclonal Antibodies Against Glycoproteins of Western Equine Encephalitis Virus," Journal of Virology, V55, pp. 840–842 (1985).
Ann R. Hunt et al., "Biochemical and Biological Characteristics of Epitopes on the Ei Glycoprotein of Western Equine Encephalitis Virus," Virology, V142, pp. 334–346 (1985).
Kiichi Yamamoto, "Properties of Monospecific Antibodies to the Glycoprotein of Western Equine Encephalitis Virus," Microbiol. Immunol, V30, pp. 343–351 (1986).
Robert E. Johnston et al., Alphavirues, Fields Virology, Third Edition, pp. 843–898 (1996).
Biwen Xu et al., "A Single Chain Fv Specific Against Western Equine Encephalitis Virus," HYBRIDOMA, V18, No. 18, pp. 315–323 (1999).
Charles E. Calisher et al, "Reevaluation of the Western Equine Encephalitis Antigenic Complex of Alphaviruses (Family Togaviridae) as Determined by Neutralized Tests," Am. J. Trop. Med Hyg., V38(2), pp. 447–452 (1988).
Melissa C. Long et al, "Pharmacokinetics Study of a Novel Chimeric Single–Chain Variable Fragment Antibody Against Western Equine Encephalitis Virus," Hybridoma, V20, No. 1, pp. 1–10 (2001).
Melissa C. Long et al., "Construction and Characterization of Monoclonal Antibodies Against Western Encephalitis Virus," HYBRIDOMA, V19, No. 2, pp. 121–127.

* cited by examiner

Primary Examiner—Laurie Scheiner
Assistant Examiner—Jeffrey S. Parkin
(74) Attorney, Agent, or Firm—Rader, Fishman & Grauer PLLC

(57) ABSTRACT

Construction and characterization of mouse monoclonal antibodies against western equine encephalitis virus (WEE) for potential use in detection, diagnosis, and immunotherapy are disclosed. Antibodies were prepared from hybridoma cells and further characterized by ELISAs, Western blotting, isotyping, and immunoprecipitation. The antibodies were also tested for cross-reactivity to other alphaviruses, such as Sindbis virus (SIN), Venezuelan equine encephalitis virus (VEE), and eastern equine encephalitis (EEE). All antibodies bound to WEE antigen in ELISAs, whereas only a subgroup of antibodies was found to be active in Western blotting and immunoprecipitations. A subset of antibodies was found to cross-react with other alphaviruses, such as SIN, VEE, and EEE.

3 Claims, 3 Drawing Sheets

CONSTRUCTION AND CHARACTERIZATION OF MONOCLONAL ANTIBODIES AGAINST WESTERN EQUINE ENCEPHALITIS VIRUS

FIELD OF THE INVENTION

This invention relates to the construction and characterization of mouse monoclonal antibodies against western equine encephalitis virus (WEE) expressed from hybridoma cell lines.

BACKGROUND OF THE INVENTION

List of Prior Art Literatures

Cao Y and Suresh M R, *Bispecific antibodies as novel bioconjugates*. Bioconjug Chem 1998;9:635–644.

Boere W A M, Benaissa-Trouw B J, Harmsen M, Kraaijeveld C A, and Snippe H, *Neutralizing and non-neutralizing monoclonal antibodies to the $E_2$ glycoprotein of semiliki forest virus can protect mice from lethal encephalitis*. J Gen Virol 1983;64:1405–1408.

Griffin D, Levine B, Tyor W, Ubol S, and Despres P, *The role of antibody in recovery from alphavirus encephalitis*. Immunol Rev 1997;159:155–161.

Hahn C S, Lustig S, Strauss E G, and Strauss J H, *Western equine encephalitis virus is a recombinant virus*. Proc Natl Acad Sci USA 1988;85:5997–6001.

Harlow E and Lane D, *Antibodies: A laboratory manual*. Cold Spring Harbor Laboratory. Cold Spring Harbor Laboratory, Cold Spring Harbor, N.Y., 1988.

Hayden M S, Gilliland L K, and Ledbetter J A, *Antibody engineering*. Curr Opin Immunol 1997;9:201–212.

Hunt A R and Roehrig F T, *Biochemical and biological characteristics of epitopes on the E1 glycoprotein of western equine encephalitis virus*. Virology 1985;142:334–346.

Johnston R E and Peters C J, *Alphaviruses*. In: *Fields Virology*, 3rd ed. Fields B N, Knipe D M, and Howley P M (Eds.). Raven Publishers, Philadelphia, 1996, pp. 843–898.

Laurino J P, Shi Q, and Ge J, *Molecular antibodies, antigens, and molecular diagnostics: a practical overview*. Ann Clin Lab Sci 1999; 29:158–166.

Long M C, Jager S, Mah D C W, JeBailey L, Mah M A, Masri S A, and Nagata L P, *Construction and characterization of a novel recombinant single chain variable fragment antibody against western equine encephalitis virus*. Hybridoma 2000;19:1–13.

Mathews J H and Roehrig J T, *Determination of the protective epitopes on the glycoproteins of venezuelan equine encephalomyelitis virus by passive transfer of monoclonal antibodies*. J Immunol 1982;129:2763–2767.

Netolitzky D L, Schmaltz F L, Rayner G A, Parker M D, Fisher G R, Bader D E, and Nagata L P, *Complete genomic RNA sequence of western equine encephalitis virus (strain 71V-1658) and expression of the structural genes*. J Gen Virol 2000;81:151–159.

Rice S A, Long M C, Lam V, and Spencer C A, *RNA polymerase II is aberrantly phosphorylated and localized to viral replication compartments following herpes simplex virus infection*. J Virol 1994;68:988–1001.

Schlesinger S and Schlesinger M J: Togaviridae, *The viruses and their replication*. In: *Fields Virology*, 3rd ed. Fields B N, Knipe D M, and Howley P M (Eds.). Raven Publishers, Philadelphia, 1996, pp. 843–898.

Strauss J H and Strauss E G, *The Alphaviruses: gene expression, replication, and evolution*. Microbiol Rev 1994;58:491–562.

Strauss J H, Strauss E G, and Kuhn R J, *Budding of alphaviruses*. Trends Microbiol 1995; 3:346–350.

Verma R, Boleti E, and George A J T, *Antibody engineering: Comparison of bacterial, yeast, insect, and mammalian expression systems*. J Immunol Methods 1998;216:165–181.

Winter G and Milstein C, *Man-made antibodies*. Nature 1991; 349:293–299.

Wright A, Shin S-U, and Morrison S L, *Genetically engineered antibodies*. Crit Rev Immunol 1992; 12:125–168.

Xu B, Kriangkum J, Nagata L P, Fulton R E, and Suresh M R, *Generation and characterization of a single chain Fv specific against western equine encephalitis virus*. Hybridoma 1999; 18:315–323.

Yamamoto K, *Properties of monospecific antibodies to the glycoprotein of western equine encephalitis virus*. Microbiol Immunol 1986;30:343–351.

Yamamoto K, Hashimoto K, Chiba J, and Simizu B, *Properties of monoclonal antibodies against glycoproteins of western equine encephalitis virus*. J Virol 1985; 55:840–842.

Western equine encephalitis virus (WEE) is an enveloped positive-sense, single-stranded RNA virus belonging to the alphavirus genus. The 12 kb genome of WEE encodes for nonstructural (5' end) and structural (3' end) proteins. The structural proteins are translated from a subgenomic mRNA (26S mRNA) as a polyprotein that is processed by viral and cellular proteases into E1 (53 kDa), E2 (47 kDa), nucleocapsid [NC] (30 kDa), E3 (10 kDa), and 6K (6 kDa) proteins. The E1 and E2 proteins are glycoproteins present in the lipid envelope. The E3 protein is also a glycoprotein that is most often not a component of the virion, but is required for infectivity in wild-type virus. The NC protein encloses the RNA genome in an icosahedral structure. The 6K protein is virion associated and promotes efficient virus assembly (reviewed in Strauss and Strauss, 1994; Strauss et al., 1995; Johnston and Peters, 1996; Schlesinger and Schlesinger, 1996).

WEE is localized to the Western hemisphere and poses a serious hazard to human health. Virus transmission is by infected mosquitoes, causing disease in humans and horses. Symptoms of WEE infection in humans include encephalitis, convulsions, paralysis, malaise, fever, headaches, nausea, and vomiting. The case fatality rate in humans is 2% to 7%. Currently, there are no known antiviral drugs effective against WEE. Although inactivated WEE vaccine exist for use in limited populations such as laboratory personnel who are at high risk of exposure to the virus, the immunogenicity of the inactivated WEE vaccine is often poor and the immunity is short-lived. Better protection against WEE is required (Johnston and Peters, 1996).

Alphavirus antigenic properties and antibody neutralization have been studied with anti-alphavirus antibodies from mouse immunoglobulins. Murine antibodies capable of neutralizing virus have been generated against E1 and E2 (Mathews and Roehrig, 1982; Boere et al., 1983; Yamamoto et al., 1985; Yamamoto, 1986). Mice were protected from challenge with WEE and Venezuelan equine encephalitis virus (VEE) when injected with antibodies against E1 and E2 in passive immunization studies (Mathews and Roehrig, 1982; Hunt and Roehrig, 1985; Yamamoto, 1986). Anti-E2 monoclonal antibodies were able to protect mice from lethal injections of Semliki Forest virus (SFV) (Boere et al., 1983). Furthermore, neutralizing and non-neutralizing antibodies to E1 and E2 administered to mice, before or after infection with virus, were protected from Sindbis virus (SIN) (Griffin et al., 1997).

Animal antisera and monoclonal antibodies provide important sources of antibody. Although recombinant antibodies have the advantages of being produced quickly, economically, and in large quantities (Wright et al., 1992; Hayden et al., 1997; Verma et al., 1998), recombinant antibodies grown in bacterial systems are often improperly folded and nonglycosylated (Wright et al., 1992; Verma et al., 1998). One may favor the use of monoclonal antibodies over recombinant antibodies for a variety of reasons. Hybridoma technology is able to provide a wide range of monoclonal antibodies that bind to different antigens with high specificity and affinity (Winter and Milstein, 1991; Laurino et al., 1999). Furthermore, monoclonal antibodies can be isolated with high purity (Winter and Milstein, 1991; Laurino et al., 1999). Accordingly, production of monoclonal antibodies directed against WEE is desirable.

Up until recently, only a limited number of monoclonal antibodies against WEE existd and have not been fully characterized. For instance, monoclonal antibodies produced by Hunt and Roehrig (1985) are capable of immunoprecipitating the E1/E2 heterodimer, identifying antigenic determinants on E1, and protecting mice when challenged with WEE. Monoclonal antibodies produced by Yamamoto et al. (1985), showing specificity for E1 and E2 in enzyme-linked immunosorbent assays (ELISA), demonstrate neutralizing activity and are found effective in passive immunization studies (Yamamoto et al., 1985; Yamamoto, 1986). Recently, there have been studies directed to specific recombinant antibodies against WEE. For example, Xu et al. (1999) successfully cloned an anti-WEE scFV. In addition, use of recombinant antibodies to histologically stain the cells expressing WEE antigens was reported in Netolitzky et al. (2000). Accordingly, it is advantageous to produce and characterize a group of monoclonal antibodies for use in detecting and diagnosing WEE effectively. It is also advantageous to study the interactions between monoclonal antibodies with other alphaviruses, such as VEE and SIN.

SUMMARY OF THE INVENTION

The present invention is directed to the construction and characterization of a group of mouse monoclonal antibodies against WEE.

An object of the present invention is to produce and identify specific monoclonal antibodies displaying various immunological activities against WEE.

Another object of the present invention is to construct and characterize monoclonal antibodies capable of cross-binding to multiple alphaviruses.

It is another object of the present invention to manufacture recombinant antibodies for hydridoma clones expressing anti-WEE monoclonal antibodies.

It is yet a further object of the present invention to use the identified monoclonal antibodies for immunodetection and immunotherpy.

According to one aspect of the present invention, it provides monoclonal antibodies against WEE expressed from hybridomas.

According to another aspect of the present invention, it provides for the construction of recombinant monoclonal antibodies from hybridoma clones against WEE, consisting of the steps of immunizing mice with antigens prepared from WEE infected cells; fusing and cloning hydridoma cells lines from the immunized mice; and genetic engineering recombinant antibodies from said cultured hybridoma cells.

DETAILED DESCRIPTION OF THE INVENTION

Figure 1:
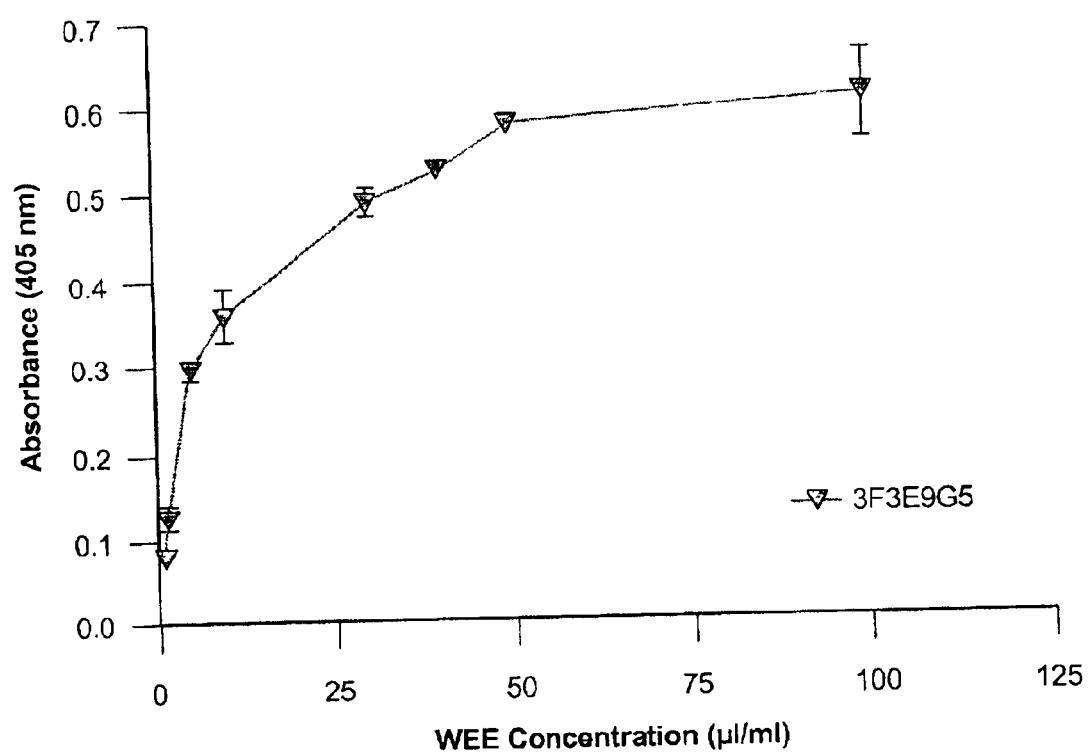
FIG. 1. WEE indirect ELISA with increasing amounts of antigen. Varying amounts of inactivated WE antigen were immobilized onto 96 well plates, after which 20 $\mu$g/ml purified 3F3E9G5 antibody was added to each of the wells. Binding was detected with horseradish peroxidase-conjugated antibodies and ABTS solution. The plates were read at an absorbance of 405 nm.
Figure 2:
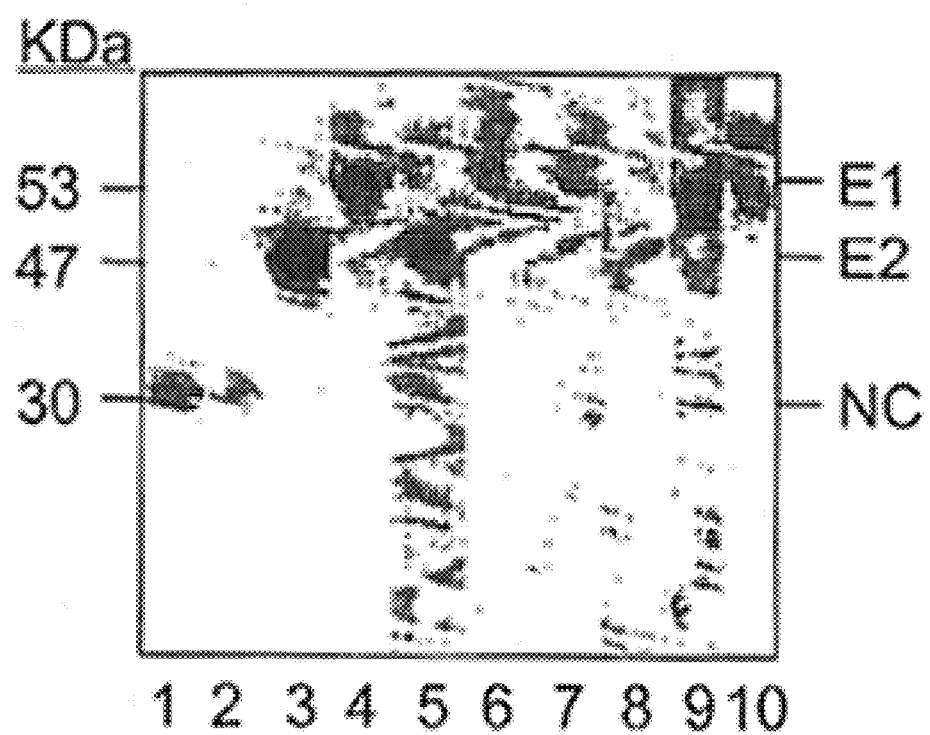
FIG. 2. Western blot analyses with WEE antibodies. Inactivated WEE antigen was run on SDS-PAGE gels (12%) and immunoblotted. The samples were probed with various WEE antibodies, Lanes: (1) 2D1E11F8; (2) 11H9E2C12; (3) 9B10D4D11G4; (4) 10A7D10F5; (5) 3F3E9G5; (6) 3F6E3F8; (7) 1G6C1H5; (8) 10B5E7E2; (8) 10B5E7E2; (9) 11D2E11F2; (10) 5F11F2G11.
Figure 3:
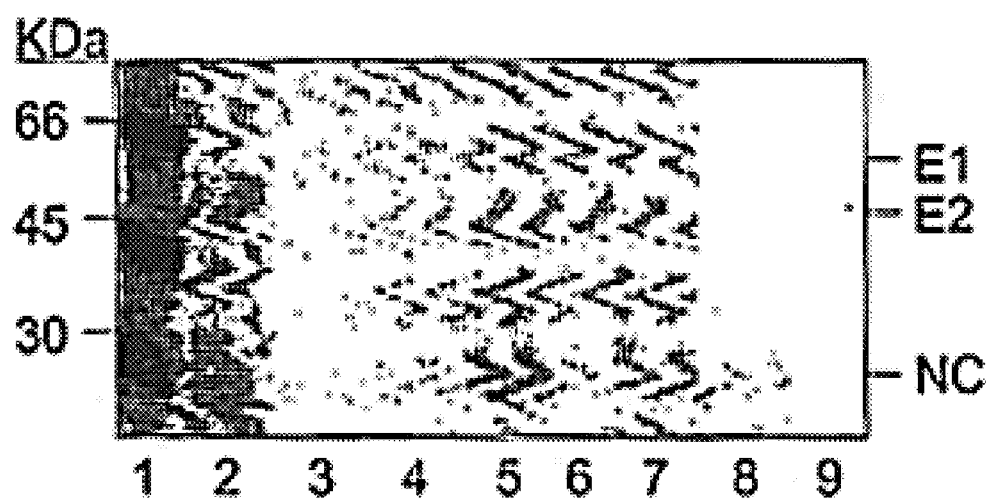
FIG. 3. Immunoprecipitation of WEE proteins. In vitro translated WEE proteins were synthesized from pCXH-3 and rabbit reticulocyte lysate in the presence of [$^{35}$S]-methionine. Radiolabeled proteins were immunoprecipitated with antibodies and protein G-agarose, run on SDS-PAGE gels (12%), and analyzed by autoradiography. Lanes: (1) MW markers; (2) in vitro synthesized WEE proteins; (3) 10B5E7E2; (4) 10A7D10F5; (5) 11H9E2C12; (6) no antibody control; (7) 3F3E9G5; (8) 8F8D2F7E11; (9) 5C5A1H11.

Materials and Methods
Preparation of Mouse Monoclonal Hybridoma Cell Lines

Mice (BALB/c, Charles River) were immunized with three doses of 20 $\mu$g of gradient purified, formalin inactivated antigen prepared from WEE strain B11 infected Vero cells (CCL-81, American Type Culture Collection, Manassa, Va.), as previously described (Xu et al., 1999; Long et al., 2000), and 50 $\mu$L TiterMax® (CytRx Corp., Norcross, Ga.) adjuvant in a total volume of 100 $\mu$L. The injections were given intraperitoneally at three week intervals. Three weeks after the third injection, the mice were given 10 $\mu$g of inactivated WEE antigen intravenously, in a total volume of 50 $\mu$l in phosphate-buffered saline (PBS). The fusions were performed on spleen cells 5–7 days later. Fusions, initial screening, and subcloning were performed by the Hybridoma Facility, Southern Alberta Cancer Research Centre, University of Calgary, Calgary, Alberta. Hybridoma cell lines were grown and maintained in RPMI 1640 media supplemented with 10% heat-inactivated fetal calf serum, 2 mM L-glutamine, 1× vitamins solution, antibiotic/antimycotic solution (100 units/ml penicillin G, 100 $\mu$g/ml streptomycin, and 25 $\mu$g/ml amphotericin B), 100 $\mu$M non-essential amino acids, and 1 mM sodium pyruvate. All tissue culture reagents were purchased from Gibco BRL, Gaithersburg, Md. The hybridoma cells were maintained at a density of 0.5–1.0×10$^6$ cells/ml and doubled approximately every 24 hr.

Purification of Antibodies

Various hybridoma clones producing anti-WEE antibodies (3F3E9G5, 5C5A1H11, 9B10D4D11G4, 10B5E7E2, 11H9E2C12) were cultured in growth media in T150 flasks. Media supernatants were collected at 24 hr time points and used as starting material for antibody purification. The supernatants were passed over protein G columns (Pierce, Rockford, Ill.), which were subsequently washed with ImmunoPure® binding buffer (Pierce). Bound IgG was eluted with ImmunoPure® elution buffer (Pierce) and six 1 ml fractions were collected. All fractions were neutralized with 100 µl of 1 M Tris-HCl pH 7.5 and monitored by absorbance at 280 nm. All antibodies eluted in fractions 3 and 4. The eluted antibodies were further desalted using Excellulose™ columns (Pierce) equilibrated in PBS pH 7.5. Concentrations of antibodies eluted were determined by absorbance (280 nm) measurements (1 mg/ml IgG=$A_{280}$/1.44).

WEE Indirect ELISA

The WEE indirect enzyme-linked immunosorbent assay (ELISA) was performed as described by Long et al., 1999. In brief, inactivated antigen from WEE strain B11 infected Vero CCL-81 cells was prepared by previous methods (Xu et al., 1999; Long et al., 2000). Varying concentrations of inactivated WEE antigen or BSA were immobilized onto Nunc Maxisorp™ flat bottomed 96 well plates (Gibco BRL). The wells were blocked, washed, and then incubated with mouse monoclonal antibodies for 1 hr at 37° C. The antibodies were diluted to various concentrations in wash buffer consisting of PBS, 0.05% Tween 20, and 0.1% BSA. The wells were subsequently washed and incubated for 1 hr at 37° C. with secondary antibody, horseradish peroxidase-conjugated goat anti-mouse antibody, at a 1:3,000 dilution in wash buffer. The plates were washed and incubated with a 1:1 solution of 2,2'-azino-bis(3-ethylbenzothiazoline-6-sulfonic acid) diammonium salt (ABTS) and hydrogen peroxide (Kirkegaard and Perry Laboratories, Inc., Gaithersburg, Md.). The plates were read at an absorbance of 405 nm.

Western Blotting of WEE

Western blotting was performed as described previously (Rice et al., 1994; Long et al., 2000). In brief, 50 µg formalin inactivated WEE antigen (described above) was separated by sodium dodecyl sulfate polyacrylamide gel electrophoresis (SDS-PAGE). WEE proteins were separated on a 12% discontinuous polyacrylamide gel, after which proteins were transferred from the gel to Immobilon™-P membranes (0.45 µm pore size, PVDF filter type) (Millipore, Bedford, Mass.). The filters were blocked, washed in PBS containing 0.1% Tween 20 and 0.02% SDS, and then probed with anti-WEE mouse monoclonal antibodies for 1 hr at room temperature. The Mini-Protean® II multi-screen apparatus (Bio-Rad Laboratories, Mississauga, Ontario) was used to analyze multiple antibody samples per immunoblot. The primary antibodies used were different dilutions of culture supernatants or different concentrations of purified protein in wash buffer. These blots were washed and incubated with a 1:3,000 dilution of horseradish peroxidase-conjugated goat anti-mouse immunoglobulin (H+L) (Caltag Laboratories, Burlingame, Calif.) for 1 hr at room temperature. Proteins were detected using the enhanced chemiluminescence (ECL) method (Amersham Pharmacia Biotech, Baie D'Urfé, Québec).

Isotyping Antibodies

Isotyping of the antibodies was performed using the monoclonal antibody-based mouse immunoglobulin isotyping kit (Pharmingen, Mississauga, Ontario). Specific rat anti-mouse antibodies ($IgG_1$, $IgG_{2a}$, $IgG_{2b}$, $IgG_3$, IgM, IgA, Ig κ, and Ig λ) were coated onto Nunc Maxisorp™ flat bottomed 96 well plates. The wells were washed with PBS containing 0.05% Tween-20 and blocked with PBS containing 1% BSA for 30 min at room temperature. Supernatants of anti-WEE hybridoma cells or purified anti-WEE antibodies were then added to the wells and incubated for 1 hr at room temperature. The wells were subsequently washed and incubated with alkaline phosphatase-conjugated rat anti-mouse Ig antibody for 1 hr at room temperature. After washing, detection of the plates was performed by incubating the wells with phosphatase substrate solution for 30 min at 37° C. The isotypes of the antibodies were determined by identifying positive yellow reactions, corresponding to specific antibody isotypes. In addition, antibody isotypes were confirmed using alternate isotyping kits from Cedarlane Laboratories Ltd., Hornby, Ontario and Gibco BRL.

Immunoprecipitation of WEE

WEE proteins were prepared in one-step in vitro transcription and translation reactions using the TNT® coupled system (Promega Corporation, Madison, Wis.). In the presence of rabbit reticulocyte lysate, transcription of the pCXH-3 plasmid resulted in WEE RNA. The pCXH-3 plasmid was constructed by cloning the entire WEE 26S region into pCI (Promega) at the XbaI and SmaI restriction sites. The WEE 26S region was placed under the control of the T7 RNA polymerase promoter and the cytomegalovirus enhancer/promoter (Netolitzky et al., 2000). The RNA was translated in the presence of [$^{35}$S]-methionine to produce radiolabeled WEE proteins, which were further processed with canine pancreatic microsomal membranes. All components of the in vitro transcription and translation reactions were incubated together for 90 min at 30° C.

The TNT® reactions were diluted to a volume of 500 µl with RIP buffer consisting of 0.15 M sodium chloride, 0.1% SDS, 50 mM Tris-HCl pH 7.4, and 1% Triton X-100, and subjected to a preabsorption step by incubating with 75 µl of protein G-agarose (Gibco BRL) for 30 min at room temperature. The samples were centrifuged at 13,000×g for 1 min, and the supernatants were then incubated with either 100 µl of supernatants from anti-WEE hybridoma cells or 20 µg of purified anti-WEE antibodies. The reactions were incubated for 1.5 hr at room temperature, after which 75 µl of protein G-agarose was added. The reactions were incubated for an additional 30 min at room temperature. Immunoprecipitated proteins were collected by centrifuging at 13,000×g for 1 min. The pellets were washed with 500 µl of RIP buffer and centrifuged at 13,000×g for 1 min; this step was repeated three additional times. The pellets were resuspended in 2x Tricine sample buffer (Bio-Rad Laboratories) containing fresh 2% β-mercaptoethanol and heated at 100° C. for 10 min. The samples were centrifuged at 13,000×g for 1 min, and the supernatants were collected. The immunoprecipitated [$^{35}$S]-labeled WEE proteins were further analyzed by SDS-PAGE and autoradiography. Radiolabeled [$^{14}$C]-molecular weight markers from Amersham Pharmacia Biotech were also run on the polyacrylamide gels.

Results

Preparation of Mouse Monoclonal Hybridoma Cell Lines and Purification of Antibodies A total of 24 hybridoma cell lines which reacted with inactivated WEE antigen in ELISA assays were isolated. Of the 24 cell lines, 17 were chosen for further in-depth analysis (Table 1). A select number of anti-WEE antibodies (3F3E9G5, 3F6E3F8, 9B10D4D11G4, 10B5E7E2, 8F8D2F7E11, 11D2E11F2, and 11H9E2C12) were purified using protein G columns. In all purifications, concentrations of antibody were highest in fractions 3 and 4, ranging from 1 to 2 mg/ml.

Antigen Binding Activity of Antibodies

The present study first sought to determine the antigen binding activity of monoclonal antibodies using the indirect ELISA assay. WEE antigen (10 $\mu$g/ml) was immobilized onto 96 well plates and incubated with antibody. Absorbance values of controls, where no antigen was present, were subtracted from absorbance values for samples containing antigen. At various dilutions, each of the supernatants possessed antigen binding activity and displayed absorbance (405 nm) readings >0.154 (data not shown). The antigen binding activity of each of the antibodies is compared in Table 1, where the maximum dilutions of antibody supernatant used in ELISAs are listed. Certain antibodies (2B7C8G2, 3F3E9G5, 3F6E3F8, 5C5A5E5, and 10B5E7E2) showed strong reactivity at >1/320 dilutions, whereas other antibodies (1G6C1H5, 5C5B7H10, 5F11F2G11, and 10A7D10F5) showed weak reactivity to WEE at 1/20 dilutions. Absorbance readings were also taken with different antigen concentrations, at fixed concentrations of the 3F3E9G5 antibody (20 μg/ml) (FIG. 1). Generally, increasing concentrations of antigen resulted in gradual increasing absorbance values or antibody-antigen binding. At a concentration of 20 μg/ml antibody, the antibodies displayed a lower limit of detection of <1 μg/ml antigen. The ELISA data showed that the mouse monoclonal antibodies were functionally active, as demonstrated by their ability to bind to WEE antigen.

The study next sought to determine which WEE proteins were specifically recognized by each of the mouse monoclonal antibodies. Western blotting techniques found that a subset of antibodies were capable of detecting WEE proteins (FIG. 2). The antibodies 1G6C1H5, 3F6E3F8, 5F11F2G11, 10A7D10F5, and 11D2E11F2 recognized E1 at approximately 53 kDa (FIG. 2, lanes 7, 6, 10, 4, and 9 respectively), whereas the antibodies 3F3E9G5, 9B10D4D11G4, and 10B5E7E2 recognized E2 at approximately 47 kDa (FIG. 2, lanes 5, 3, and 8 respectively). It is important to note that it is difficult to distinguish between E1 and E2, as both proteins often comigrate on 12% polyacrylamide gels. The 30 kDa nucleocapsid (NC) is recognized by 2D1E11F8 and 11H9E2C12 (FIG. 2, lanes 1 and 2 respectively). WE proteins were not detected by the antibodies 2B7C8G2, 2H1D12E2, 5C5A1H11, 5C5A5E5, 5C5B7H10, 5C5C7C4, and 8F8D2F7E11 by Western blotting, although WEE proteins were detected by these particular antibodies in ELISAs. This may be because the ELISA is more sensitive than the Western blot. Furthermore, antibodies detected "native" WEE proteins in an ELISA, as opposed to "denatured" WEE proteins in a Western blot. To further characterize each of the mouse monoclonal antibodies, the isotypes of the antibodies were determined (Table 1). The antibodies displayed $IgG_1$, $IgG_{2a}$, or $IgG_{2b}$ isotypes; none of the antibodies showed, $IgG_3$, IgA, and IgM isotypes. Most of the antibodies were either $IgG_1$ or $IgG_{2a}$, with kappa light chains. One antibody, 11H9E2C12, was $IgG_{2b}$ with lambda light chains. The isotyping data provided information for immunoprecipitation experiments. Protein G was used to immunoprecipitate the antibody-antigen complexes since protein A does not have strong affinity for the mouse IgG, subclass (Harlow and Lane, 1988). For antibodies displaying $IgG_{2a}$ and $IgG_{2b}$ isotypes, additional immunoprecipitation experiments were done with protein A.

Immunoprecipitation experiments were performed to demonstrate that the antibodies were capable of binding to native WEE proteins. It was found that only a limited number of antibodies were capable of immunoprecipitating WEE proteins with protein G agarose (FIG. 3). In vitro translated E1, E2, and NC were first produced from the TNT® system (FIG. 3, lane 2). The bands for E1 and E2 run together. Furthermore, the NC runs as a broad band. The antibodies 10A7D10F5 and 8F8D2F7E11 weakly immunoprecipitated E1 (FIG. 3, lanes 4 and 8 respectively), whereas the antibodies 3F3E9G5 and 5C5A1H11 immunoprecipitated E2 (FIG. 3, lanes 7 and 9 respectively). Lastly, 11H9E2C12 immunoprecipitated the NC (FIG. 3, lane 5). No WEE proteins were immunoprecipitated with 10B5E7E2 (FIG. 3, lane 3), in the absence of antibody (FIG. 3, lane 6), or with protein A (data not shown). All other antibodies did not show any immunoprecipitation activity, although they displayed ELISA activity. This may be due to immunoprecipitations being less sensitive than ELISAs. Interestingly, 5C5A1H11 and 8F8D2F7E11 were able to immunoprecipitate WEE proteins but not able to detect WEE proteins by Western blotting. The antibodies may be capable of detecting WEE proteins in proper conformation in an immunoprecipitation but not WEE proteins as linear epitopes in Western blotting. Certain antibodies, 3F3E9G5, 10A7D10F5, and 11H9E2C12 were able to recognize both "native" and "denatured" proteins as they showed positive reactivity to WEE antigen in ELISA, Western blotting, and immunoprecipitations.

Lastly, cross-reactivity experiments were performed in order to determine if the anti-WEE antibodies displayed binding activity to other alphaviruses. Antigen from SIN, VEE, or EEE was immobilized onto ELISA plates and incubated with antibody. Several antibodies, 3F3E9G5, 9B10D4D11G4, and 11D2E11F2, cross-reacted with SIN antigen, whereas other antibodies 2B7C8G2, 2D1E11F8, 5C5A1H11, and 11H9E2C12 reacted with EEE (Table l). The 11H9E2C12 antibody bound not only to WEE and EEE, but also VEE.

Discussion

Protection from WEE infection and disease are relevant and important issues affecting a large number of the population. It has been found that in mice, protection from alphavirus by activated T cells alone is not effective or sufficient. Instead, clearance and protection from infectious virus in the nervous system are accomplished by delivered antibodies (Griffin et al., 1997). Thus, an important method for protection against WEE may be facilitated by passive immunization, where viral-specific antibodies are administered to help prevent illness or mediate recovery of individuals exposed to virus. A limited number of monoclonal antibodies with both neutralization and passive immunization activity against alphaviruses have been previously found (Mathews and Roehrig, 1982; Boere et al., 1983; Yamamoto, 1986; Johnston and Peters, 1996; Griffin et al., 1997). The present study reports the construction and characterization of a collection of mouse monoclonal antibodies capable of recognizing WEE proteins for potential use in identification and therapy studies.

The 24 hybridomas expressing different anti-WEE antibodies are isolated, and the most reactive antibodies are evaluated further. The monoclonal antibodies all show varying reactivity to WEE in ELISAs, both with the supernatants and with the purified fractions. The antibodies 2B7C8G2, 3F3E9G5, 3F6E3F8, 5C5A5E5, and 10B5E7E2, display the highest binding activity to WEE, at dilutions >1/320. Others display binding activity at dilutions >1/100. Detection of WEE antigen by 3F3E9G5 is sensitive to less than 1 μg/ml when 20 μg/ml of antibody is used. These antibodies are strong candidates for use in ELISA based WEE detection assays. Of these antibodies listed, only 3F3E9G5 (E2), 3F6E3F8 (E1), and 10B5E7E2 (E2) are reactive against WEE protein in Western blotting. Furthermore, of these three antibodies, only 3F3E9G5 is reactive in immunoprecipitations. From these results, it appears that of the strongly binding WEE antibodies, 3F3E9G5 is the most versatile antibody, capable of recognizing WEE proteins in "native" and "denatured" forms and in a number of different assays.

Many of the antibodies, 1G6C1H5 (E1), 2D1E11F8 (NC), 3F3E9G5 (E2), 3F6E3F8 (E1), 5F11F2G11 (E1), 9B10D4D11G4 (E2), 10A7D10F5 (E1), 10B5E7E2 (E2), 11D2E11F2 (E1), and 11H9E2C12 (NC) display activity in Western blotting and recognize WEE proteins with clear resolution. The antibodies 3F3E9G5, 10A7D10F5, and 11H9E2C12 are not only capable of recognizing WEE proteins in Western blotting but also in immunoprecipitations, indicating that these three antibodies may be capable of recognizing E2, E1, and NC respectively in not only "denatured" but also "native" forms. 5C5A1H11 (E2) and 8F8D2F7E11 (E1) may only recognize WEE proteins in their "native" forms, as these antibodies are reactive only in ELISAs and immunoprecipitations but not in Western blotting.

The monoclonal antibody against western equine encephalitis virus, reference no. 8F8D2F7E11, has been deposited at the International Depositary Authority of Canada, National Microbiology Laboratory, Health Canada, at 1015 Arlington Street, Winnipeg, Manitoba, Canada R3E 3R2 on Jan. 13, 2004 and was assigned Accession No. 120104-01.

A subgroup of the anti-WEE antibodies is also capable of binding to other alphavirus antigens. The antibodies 3F3E9G5, 9B10D4D11G4, and 11D2E11F2 bind to SIN, whereas 2B7C8G2, 2D1E11F8, and 5C5A1H11 bind to EEE. One antibody, 11H9E2C12, recognizes three different alphaviruses, WEE, VEE, and EEE. This is not entirely surprising as a large number of viruses in the alphavirus genus are closely related in terms of molecular characteristics and structure (Strauss and Strauss, 1994; Johnston and Peters, 1996). For instance, alphavirus nucleocapsids are antigenically similar. The nuclecapsid gene of WEE is closely related to the analogous regions of EEE (Hahn et al., 1988). Interestingly, 2D1E11F8 and 11H9E2C12, antibodies which recognize the nucleocapsid of WEE, bind to EEE. The E1 and E2 sequences of WEE are most closely aligned with comparable sequences of SIN (Hahn et al., 1988). This study also finds that 3F3E9G5, 9B10D4D11G4, and 11D2E11F2 bind to one of the WEE glycoproteins and is cross-reactive with SIN. Because the above antibodies recognize other alphaviruses in addition to WEE, the antibodies may potentially have functions in multiple systems, not only in WEE based assays but also in SIN, VEE, and EEE immunodetections and immunotherapies.

The information derived from the characterization of the mouse monoclonal antibodies may be used in further immunological studies. These antibodies can be used to detect WEE in a number of forms, as the antibodies have different specificities and reactivities in various assays. Recombinant antibodies such as scFv, Fab, and bispecific antibodies, can be constructed from each of the hybridoma clones expressing anti-WEE monoclonal antibodies. From the hybridoma expressing 10B5E7E2, a scFv retaining good recognition to the WEE antigen was constructed. This scFv was fused to the human IgG, heavy chain to produce a chimeric antibody which may show potential for immunotherapy (Long et al., 2000). These recombinant antibodies along with the mouse monoclonal antibodies can serve in a wide range of applications, ranging from immunohistochemistry immunoassays, radioimmunodiagnosis, radioimmunotherapy, and immunotherapy (Hayden et al., 1997; Cao and Suresh, 1998).

It is to be understood that the embodiments and variations shown and described herein are merely illustrative of the principles of this invention and that various modifications may be implemented by those skilled in the art without departing from the scope and spirit of the invention.

TABLE 1

Monoclonal anitbody specificities, isotypes, and cross-reactivities

| ANTIBODY | WESTERN AND IMMUNO-PRECIPITATION SPECIFICITY | ELISA | FUSION PARTNER | Isotyping | | | | | Crossreactivity | | |
|---|---|---|---|---|---|---|---|---|---|---|---|
| | | | | $IgG_1$ | $IgG_{2a}$ | $IgG_{2b}$ | Kappa | Lambda | SIN | VEE | EEE |
| 1G6C1H5 | E1 | 1/20 | Sp2/mIL-6 | + | | | + | | | | |
| 2B7C8G2 | — | >1/320 | P3/NSI/1Ag-1-NSI | + | | | + | | | | + |
| 2D1E11F8 | NC | 1/80 | P3/NSI/1Ag-1-NSI | + | | | + | | | | + |
| 2H1D12E2 | — | 1/40 | P3/NSI/1Ag-1-NSI | + | | | + | | | | |
| 3F3E9G5 | E2 | >1/320 | Sp2/mIL-6 | + | | | + | | + | | |
| 3F6E3F8 | E1 | >1/320 | Sp2/mIL-6 | | + | | + | | | | |
| 5C5A1H11 | E2 | 1/160 | P3/NSI/1Ag-1-NSI | + | | | + | | | | + |
| 5C5A5E5 | — | >1/320 | P3/NSI/1Ag-1-NSI | + | | | + | | | | |
| 5C5B7H10 | — | 1/20 | P3/NSI/1Ag-1-NSI | + | | | + | | | | |
| 5C5C7C4 | — | 1/40 | P3/NSI/1Ag-1-NSI | + | | | + | | | | |
| 5F11F2G11 | E1 | 1/20 | P3/NSI/1Ag-1-NSI | + | | | + | | | | |
| 8F8D2F7E11 | E1 | 1/160 | Sp2/mIL-6 | | + | | + | | | | |
| 9B10D4D11 | E2 | 1/160 | P3/NSI/1Ag-1-NSI | + | | | + | | + | | |
| 10A7D10F5 | E1 | <1/20 | Sp2/mIL-6 | | | + | + | | | | |
| 10B5E7E2 | E2 | >1/320 | Sp2/mIL-6 | | | + | + | | | | |
| 11D2E11F2 | E1 | 1/80 | Sp2/mIL-6 | | | + | + | | + | | |
| 11H9 | NC | 1/160 | P3/NSI/1Ag-1-NSI | | | + | | + | | + | + |

What is claimed is:

1. An isolated and purified monoclonal antibody (Mab) that binds specifically to the western equine encephalitis E1 glycoprotein, wherein said Mab is expressed from a hybridoma, and wherein said hybridoma is deposited with the International Depositary Authority of Canada under Accession number 120104-01.

2. The Mab according to claim 1 for use in ELISA-based WEE detection assays.

3. The Mab according to claim 1, wherein said Mab is capable of recognizing WEE proteins in "native" or "denatured" form.

* * * * *